United States Patent [19]

Gardner, Jr.

[11] E Re. 29,487

[45] Reissued Dec. 6, 1977

[54] EARPLUGS

[75] Inventor: Ross Gardner, Jr., Stoughton, Mass.

[73] Assignee: Cabot Corporation, Boston, Mass.

[21] Appl. No.: 666,364

[22] Filed: Mar. 12, 1976

Related U.S. Patent Documents

Reissue of:

[64] Patent No.: 3,811,437
Issued: May 21, 1974
Appl. No.: 192,366
Filed: Oct. 26, 1971

[51] Int. Cl.[2] ..... A61F 11/02

[52] U.S. Cl. ..... 128/152

[58] Field of Search ..... 128/152, 151; 181/23, 181/33, 126, 135

[56] References Cited

U.S. PATENT DOCUMENTS

| | | | |
|---|---|---|---|
| 2,262,568 | 11/1941 | Wade | 128/152 |
| 2,538,339 | 1/1951 | Thomas | 128/152 |
| 2,717,596 | 9/1955 | Knight | 128/152 |
| 2,824,558 | 2/1958 | Michael | 128/152 |
| 3,097,059 | 7/1963 | Hoffman | 128/152 |

FOREIGN PATENT DOCUMENTS

| | | | |
|---|---|---|---|
| 733,542 | 7/1955 | United Kingdom | 128/152 |

*Primary Examiner*—John D. Yasko
*Attorney, Agent, or Firm*—Jack Schuman; Barry R. Blaker; Lawrence A. Chaletsky

[57] ABSTRACT

There are disclosed earplugs composed of certain polymeric foam materials. The earplugs are of generally cylindrical shape and of somewhat larger diameter than the human ear canal. The earplugs are composed of a foamed plasticized polymeric material having a sufficiently high concentration of plasticizer to provide the earplug with a reduced rate of recovery from compression.

19 Claims, 3 Drawing Figures

EARPLUGS

Matter enclosed in heavy brackets [ ] appears in the original patent but forms no part of this reissue specification; matter printed in italics indicates the additions made by reissue.

The present invention relates generally to earplug constructions and more particularly to earplug constructions adapted for insertion into the ear canal.

Many devices are known which are adapted for insertion into the human ear canal in order to suppress or attenuate the transmission of dangerous noise and thus confer a measure of protection to the anatomical hearing apparatus. Such devices have taken many forms. For instance, perhaps the simplest earplug is formed of wadded cotton. While blessed with the benefit of simplicity, such earplugs are not normally greatly effective as acoustic barriers. In another embodiment of this simple earplug, a fibrous material, such as cotton wadding, is impregnated with a compliant waxy substance. Yet another form of earplug is composed of a shapeless, compliant, "dead soft" mineral-filled waxy substance. These ear-plugs are normally deficiant due to a lack of sufficient resiliency; thus, when deformed or compressed in order to enter the ear canal such earplugs do not normally recover or expand sufficiently so as to effectively obturate the ear canal. Still other earplugs are known which take the form of molded elastomeric structures, natural rubber being a common material of construction. Included within this class are earplugs having molded therein check valves and other substructures designed to allow normal voice tones to be transmitted therethrough while cancelling or preventing transmission of injurious overpressures. Such molded elastomer earplugs suffer from the fact that their size and shape is preordained and fixed in the molding thereof. Thus, they must initially be carefully fitted to the wearer in order to provide security, comfort and effective sound attenuation properties. Unfortunately, the size and shape of the human ear canal is quite variable amongst persons; indeed, bilateral symmetry in a single individual is often lacking. Accordingly, it is not possible to manufacture molded elastomeric earplugs of a universally useful size and shape.

In recent years there have come into extensive usage lightweight earphones or headphones comprising generally a miniature speaker having tubular member(s) extending therefrom the tips of which members are adapted for insertion in the external auditory meatus. Said tips are generally comprised of a foamed or unfoamed polymeric material such as neoprene or sponge rubber. In the case of the unfoamed polymeric tip members major deficiencies usually reside in the facts that the tip members (1) tend to slip out of the ear canal, and (2) the relatively non-compliant character of the polymeric material does not lend itself to complete obturation of the ear canal. Thus, bothersome external ambient noise can often by-pass such unfoamed tip members. In the case of sponge rubber tip members the resiliency of the sponge materials is generally excessively rapid and mitigates against actual insertion of the tip member into the ear canal proper. Such tip members are usually worn, therefore, in a manner such as to urge the respective members inwardly against the external auditory meatus. This is often found uncomfortable and, in any case, is not ordinarily efficient in blocking the ear canal.

In accordance with the present invention, however, there are provided earplug structures which substantially ameliorate or overcome the aforedescribed problems.

OBJECTS OF THE INVENTION

It is a principal object of the invention to provide novel earplugs.

It is another object of the invention to provide earplugs adapted for insertion into the ear canals with substantially complete obturation thereof.

It is another object of the invention to provide earplugs having excellent sound barrier properties.

It is another object of the invention to provide earplugs adapted for insertion into the ear canals wherein bone conduction of sound (such as through the plug and into the mastoid process) is substantially completely avoided.

It is still another object of the invention to provide novel ear insertable earpieces for lightweight earphone devices.

Other objects and advantages of the invention will in part be obvious and will in part appear hereinafter.

GENERAL DESCRIPTION OF THE INVENTION

In accordance with the present invention there are provided earplugs of generally cylindrical shape and of somewhat larger diameter than that of the human ear canal. Said earplugs are composed of a foamed polymeric material having a rate of recovery from 60 percent compression to 40 percent compression thereof of from 1 to 60 seconds and an equilibrium pressure at 40 percent compression thereof of from 0.2 to 1.3 p.s.i.

THE DRAWINGS

DETAILED DESCRIPTION OF THE INVENTION

Figure 1:
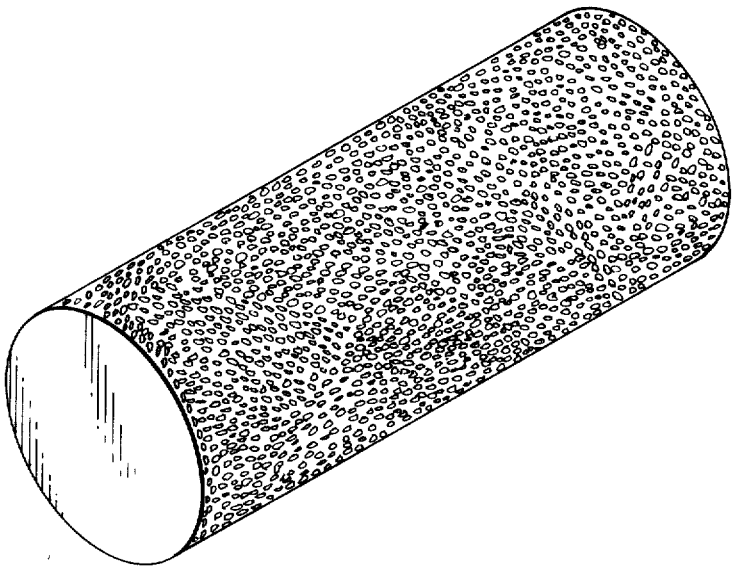
FIG. 1 is a perspective view of one embodiment of an earplug of the invention.

Referring to FIG. 1 it will be seen that the earplug of the invention is of generally cylindrical shape and has a diameter somewhat greater than that of the average adult human ear canal. For instance, a diameter of between about ⅜ inch and about ¾ inch is generally acceptable. Optimally, the diameter of the earplug will be between 9/16 inch and 11/16 inch. Further, it should be noted and understood that the term "cylindrical" as employed herein includes within its scope structures having a relatively shallow truncated cone shape or a substantially spherical shape. Where the earplug takes the form of a truncated cone, the above diameter criteria may be employed taken at the midpoint of the cone. Where the earplug is spherical, the above criteria may be applied to the diameter of said sphere.

The length of the earplug can generally be between about ½ inch to about 1 inch. At lengths substantially greater than about 1 inch, for instance, sufficient material can overhang the external ear so as to be bothersome to the wearer. Desirably, the length of the earplug will be between 7/16 and about ¾ inch.

Any flexible polymeric material which can be foamed so as to result in an ultimately formed earplug structure meeting the recovery rate and pressure criteria set forth hereinabove constitutes a satisfactory material of construction in the earplugs of the invention. Accordingly, polymers of ethylene, propylene, vinyl chloride, vinyl acetate, diisocyanate, cellulose acetate or isobutylene can all be generally employed. In particular, however, I much favor vinyl chloride homopolymers and copolymers comprising at least 85 percent by weight of vinyl chloride and up to 15 percent by weight of other monomers such as vinylidene chloride, vinyl esters of carboxylic acids, e.g., vinyl acetate, vinyl propionate, vinyl butyrate and vinyl benzoate, esters of unsaturated acids, e.g., alkyl acrylates such as methyl acrylate, ethyl acrylate, propyl acrylate, butyl acrylate, allyl acrylate, and the corresponding esters of methacrylic acid; vinyl aromatic compounds, e.g., styrene, ortho-chlorostyrene, para-chlorostyrene, 2,5-dichlorostyrene, 2,4-dichlorostyrene, paraethylstyrene, vinyl naphthalene and $\alpha$-methyl tyrene, dienes such as butadiene and chlorobutadiene, unsaturated amides such as acrylic acid amide and acrylic acid anilide; unsaturated nitriles such as acrylic acid nitrile; and esters of $\alpha,\beta$-unsaturated carboxylic acids, e.g., the methyl, ethyl, propyl, butyl, amyl, hexyl, heptyl, octyl, allyl, methallyl, and phenyl esters of maleic, crotonic and fumaric acids and the like. Such vinyl chloride based polymers, and particularly the vinyl chloride homopolymers, can normally be compounded into plastisol form with a blowing agent and a high concentration of a suitable organic plasticizer so as to result in stabilized foams having the rate of recovery and pressure characteristics necessary in the compositions from which the earplugs of the invention are fabricated.

With respect to said characteristics, it is clear that the relatively slow recovery rate in returning from 60 percent compression to 40 percent compression of the foamed materials employed in the earplug construction of the invention confers to the user the ability to initially compress or otherwise deform the earplug and provide sufficient time for insertion thereof into the ear canal. Subsequent to said insertion, the compressed or deformed earplug slowly recovers and attempts to regain its original shape. By so doing, the recovering polymeric material conforms to the structure of the ear canal and establishes substantially complete obturation thereof. In a preferred embodiment of the invention, the recovery rate of the foamed polymer composition will be between 2 and about 20 seconds.

The manner in which the recovery rate of the foamed polymer composition is determined for the purposes of the present invention is as follows:

Plugs of the polymeric foam composition are cut with a hollow tube borer, the dimensions of the plugs being about 0.630–0.640 inch in diameter and having a length of between 0.495 and 0.615 inch. A parallel plate gauge is employed having a spacing of 0.375 inch between the opposing plate surfaces. Said 0.375 inch spacing between plates thus corresponds to about 40 percent compression of the original plug diameter. A plug specimen is twirled lengthwise between the fingers for 15 to 30 seconds with an ultimate compression of the plug to about 0.25 inch in diameter, corresponding to about 60 percent reduction in the original diameter thereof. The plug is then inserted lengthwise and released between the parallel plates, the time from said release to contact of 75 percent of the linear surface of the plug with both plates being determined by stopwatch measurement. In order to maximize the relative precision of the test, a number of test specimens taken from the same sample foam are employed and the results averaged.

The 40 percent compression equilibrium pressure testing of the polymeric foam is accomplished employing the test plugs produced and employed in the above recovery rate testing procedure. In pressure testing, however, there is employed an Instron Universal Testing Instrument, Model TTC, having a parallel plate specimen holder in which the parallel plates are spaced 0.375 inch apart. The Instron is further equipped with a 1 pound load cell. Test plugs of the foamed polymeric composition are finger twirled in the manner described previously for a 30 second period and are placed lengthwise between the plates of the parallel specimen holder. When the load cell reading attains a 40 to 80 percent full scale deflection, no further specimens are added. The instrument and specimens are allowed to stand for 10 minutes in order to attain substantial equilibrium and the number of plugs and the measured total pressure are recorded. Since the contact area of each plug with the plates of the specimen holder corresponds to about 0.25 in.$^2$, the average pressure exerted by each plug specimen is determined by the equation:

$$\begin{matrix}\text{pressure (p.s.i.)}\\ \text{at}\\ \text{40\% compression}\end{matrix} = \frac{\text{total measured pressure}}{\text{No. of specimens}} \times 4$$

The pressure criteria established hereinbefore for the foamed polymeric compositions employed in the fabrication of the earplugs of the invention is also important in that the achievement of such pressure characteristics insures that the completed earplug will bear in obturating relationship against the ear canal but with insufficient pressure as to cause discomfort to the wearer. In a preferred embodiment, the foamed polymeric compositions employed in the fabrication of the earplugs of the invention will have a 40 percent compression equilibrium pressure of between 0.35 and 1.0 p.s.i.

Taken together, the pressure and recovery rate criteria of the foamed polymeric compositions also define a composition having the further characteristic of relative "deadness." Thus, while form stable in the sense that the earplug, when deformed, will tend to recover its original shape and size, the slow rate of recovery thereof and the very small overall pressure exerted by the plug surfaces on the constraining ear canal further insure the fact that little sound will be transmitted through the material and into the bony structure of the canal. This, too, is highly advantageous since substantial undesirable sound transmission by way of bone conduction through the mastoid process can occur with solid earplugs.

There follow a number of non-limiting illustrative Examples:

EXAMPLE 1

A vinyl chloride plastisol formulation was compounded employing the following ingredients:

| | Parts by Weight |
|---|---|
| Opalon 440, a general purpose homopolymer of vinyl chloride produced by Monsanto Co., St. Louis, Missouri | 115 |

-continued

| | Parts by Weight |
|---|---|
| Admex 523, an aromatic polyester plasticizer produced by Archer-Daniels-Midland Co., Minneapolis, Minnesota | 95 |
| Estynox 203, an epoxidized soya bean oil stabilizer/plasticizer produced by The Baker Castor Oil Co., Bayonne, New Jersey | 5 |
| Estynox 203, an epoxidized soya bean oil stabilizer/plasticizer produced by The Baker Castor Oil Co., Bayonne, New Jersey | 5 |
| Kempore 200, an azodicarbonamide foaming agent produced by National Polychemicals, Inc. Wilmington, Massachusetts | 8 |
| Antimony Trioxide flame retardant | 8 |
| Advastab T-150, organometallic stabilizer produced by Advance Division, Carlisle Chemical Works, Inc., New Brunswick, New Jersey | 2 |
| Houdry FS-100, a polymeric surfactant produced by Air Products and Chemicals, Inc., Philadelphia, Pennsylvania | 2 |
| Vanstay 8014, stabilizer produced by R.T. Vanderbilt Co., Inc., New York, New York | 3 |

The resulting plastisol was cast on release paper and doctor bladed to a thickness of about 77 mils. The cast plastisol was continuously conducted through an oven heated to a nominal temperature of about 420° F at a nominal residence time of about 5 minutes. The resulting foamed sheet composition had a density of about 7 lbs/ft$^3$, a rate of recovery from 60 percent compression to 40 percent compression of about 4 seconds and a 40 percent compression equilibrium pressure of about 0.78 p.s.i. When examined under 75X magnification, the foamed polymer appeared to be of predominantly closed-celled structure.

When cut into cylindrical plugs of about ⅝ inch diameter by about ⅝ inch length, the resulting structures could be finger compressed and inserted into the ear canals without difficulty. The compressed plugs thereafter recovered to substantially completely and comfortably obturate the ear canals and were found to be highly effective in attenuating the transmission of 15–15,000 Hz/sec frequencies therethrough.

Figure 2:
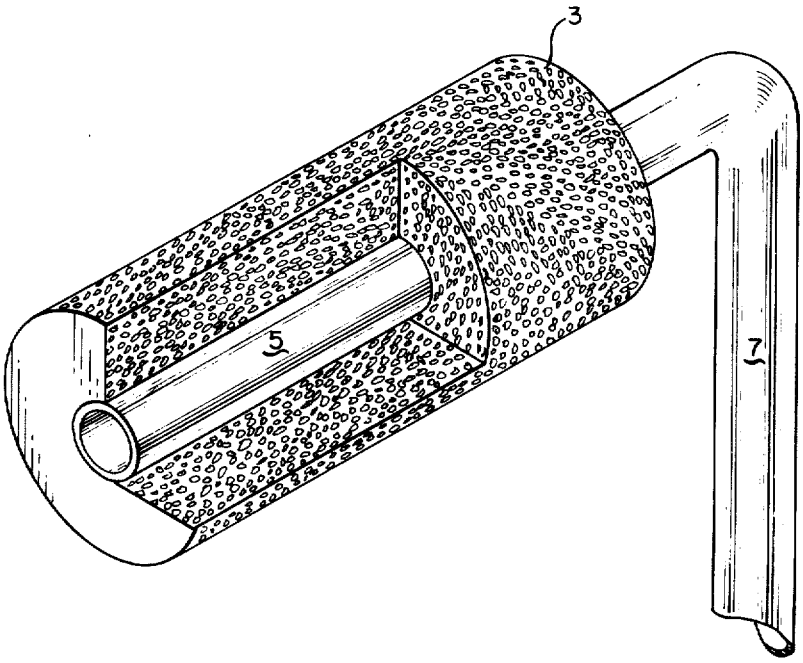
FIG. 2 is a perspective, partially sectioned view of an earpiece portion of an earphone bearing a modified foamed polymeric earplug of the invention as the external ear insertable tip member.
Figure 3:
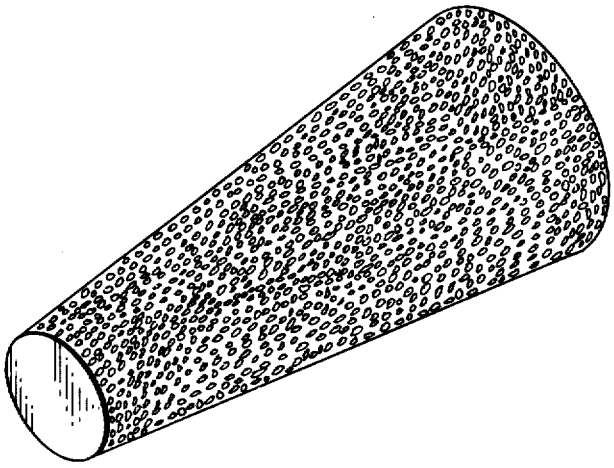
*FIG. 3 is a perspective view of another embodiment of the invention having a truncated cone shape.*

Referring now to FIG. 2, several of the earplugs are coaxially bored throughout their lengths with a central corer having a diameter of about ⅛ inch. The resulting structures are then employed as a covering 3 over tubular tip portion 5 of a lightweight headphone set (partially shown). Again, it is found that the foamed polymeric structures are compressible to below the dimensions of the ear canal and can be comfortably inserted therein with subsequent slow recovery thereof to substantially completely fill the cross-section of the ear canal. The headphone set is adjudged to be superior in wearer comfort and is highly effective in selectively conducting sound only through the tubular sound conductor 7 thereof.

EXAMPLE 2

A foamable polyvinyl chloride plastisol composition was formulated employing the following ingredients:

| | Parts by Weight |
|---|---|
| Opalon 440 | 100 |
| Admex 523 | 95 |
| Estynox 203 | 5 |
| Kempore 200 | 4 |
| Antimony trioxide flame retardant | 10 |

-continued

| | Parts by Weight |
|---|---|
| Surfex MM, a precipitated calcium carbonate filler produced by Diamond Alkali Co., Cleveland, Ohio | 15 |
| Advastab T-150 | 2 |
| Houdry FS-100 | 2 |
| Vanstay 8014 | 3 |

The resulting plastisol composition was cast on release paper and doctor bladed to a thickness of about 114 mils. The cast sheet was then continuously fed through an oven as in Example 1. The resulting foamed polyvinylchloride sheet had a density of about 13 lbs/ft$^3$, a rate of recovery from 60 percent compression to 40 percent compression of about 1 second and a 40 percent compression equilibrium pressure of about 1.32.

When cut into cylindrical structures of about ⅝ inch diameter and ⅝ inch length, the resulting wares were found to be acceptable as earplugs and could be inserted into the ear canals. However, due principally to the substantially more rapid recovery rate than the composition of Example 1, the wearer was required to insert the plugs with considerably more rapidity following compression thereof and certain of the test subjects were aware of the pressure exerted by the plugs on the ear canal.

EXAMPLE 3

Two polyvinylchloride formulations having substantially similar ingredients as employed in Examples 1 and 2 but different relative concentrations were produced. Upon testing, one of the resulting polyvinylchloride foams had a density of about 4 lbs/ft$^3$, a recovery rate from 60 percent compression to 40 percent compression of about 106 seconds and an exerted equilibrium pressure at 40 percent compression of about 0.19 p.s.i. Earplugs formed of this material were found to be deficient in that the recovery rate was excessively slow and the exerted pressure upon the ear canal was slightly below that required to completely obturate the ear canal with the foamed polymeric shape. The other foamed polyvinylchloride sheet composition was found to have an apparent density of about 6 lbs/ft$^3$, a recovery rate (60 to 40 percent compression) of about 13 seconds and an exerted equilibrium pressure at 40 percent compression of about 0.37 p.s.i. Cylindrical (including truncated cone shapes) earplugs formed of this material were found to be of excellent quality in terms of facile insertion, wearer comfort and sound attenuation properties.

While there are above described a number of specific embodiments of the present invention, it is obviously possible to produce other embodiments and various equivalent modifications thereof without departing from the spirit of the invention.

Having set forth the general nature and several preferred embodiments of the present invention, the true scope thereof is now particularly pointed out in the appended claims.

What is claimed is:

1. An earplug of generally cylindrical shape having a diameter of between ⅝ and ¾ inch, a length [to] *of* between ½ and 1 inch and composed of a resilient plasticised polymeric foam having a sufficiently high concentration of organic plasticizer therein as to provide said foam with a rate of recovery [of] *from* 60 percent compression thereof to 40 percent compression *thereof* of from 1 to 60 seconds and an equilibrium pressure [of] *at* 40 percent compression thereof of from 0.2 to 1.3 p.s.i.

2. The earplug of claim 1 wherein said polymeric foam has a rate of recovery of from 2 to 20 seconds.

3. The earplug of claim 1 wherein said polymeric foam has an equilibrium pressure at 40 percent compression of between 0.35 and 1.0 p.s.i.

4. The earplug of claim 1 wherein the polymeric constituent of said foam is a polymer of vinyl chloride.

5. The earplug of claim 1 wherein the polymeric constituent of said foam is a homopolymer of vinyl chloride.

6. The earplug of claim 1 having a diameter of between 9/16 and 11/16 inch.

7. The earplug of claim 1 having a length of between 7/16 and ¾ inch.

8. The earplug of claim 1 wherein said polymeric foam is formed from a polyvinylchloride plastisol.

9. The earplug of claim 1 having a truncated cone shape.

10. The earplug of claim 1 having a substantially longitudinal bore therethrough said bore being adapted to receive the tip portion of a sound conducting tube.

*11. An earplug having a size and shape adapted to be compressed and inserted into the human ear canal and there allowed to expand and obturate the ear canal, said earplug comprising a resilient plasticized polymeric foam having a sufficiently high concentration of organic plasticizer therein as to provide said foam with a rate of recovery from 60 percent compression thereof to 40 percent compression thereof of from 1 to 60 seconds and an equilibrium pressure at 40 percent compression thereof of from 0.2 to 1.3 p.s.i.*

*12. An earplug as in claim 11 having a generally cylindrical shape.*

*13. An earplug as in claim 11 wherein said polymeric foam has a rate of recovery from 60 percent compression thereof to 40 percent compression thereof from 2 to 20 seconds.*

*14. An earplug as in claim 11 wherein said polymeric foam has an equilibrium pressure at 40 percent compression thereof from 0.35 to 1.0 p.s.i.*

*15. An earplug as in claim 11 wherein the polymeric constituent of said foam is a polymer of vinyl chloride.*

*16. An earplug as in claim 11 wherein said polymeric foam is formed from a polyvinylchloride plastisol.*

*17. An earplug as in claim 11 having a truncated conical shape.*

*18. An earplug as in claim 11 having a bore therethrough, said bore being adapted to receive a sound conducting tube.*

*19. An earplug as in claim 18, further comprising a sound conducting tube mounted in said bore.*

* * * * *